(12) United States Patent
Sakurai

(10) Patent No.: US 8,264,470 B2
(45) Date of Patent: Sep. 11, 2012

(54) CLEANING MODE FOR INFORMATION DISPLAY DEVICE WITH TOUCHSCREEN

(75) Inventor: Yuka Sakurai, Hyogo (JP)

(73) Assignee: Panasonic Corporation, Osaka (JP)

( * ) Notice: Subject to any disclaimer, the term of this patent is extended or adjusted under 35 U.S.C. 154(b) by 511 days.

(21) Appl. No.: 12/536,555

(22) Filed: Aug. 6, 2009

(65) Prior Publication Data

US 2010/0045623 A1 Feb. 25, 2010

(30) Foreign Application Priority Data

Aug. 7, 2008 (JP) ................................. 2008-203977

(51) Int. Cl.
*G06F 3/041* (2006.01)
(52) U.S. Cl. ........................................................ 345/173
(58) Field of Classification Search .................... 345/173
See application file for complete search history.

(56) References Cited

U.S. PATENT DOCUMENTS

| | | | |
|---|---|---|---|
| 4,992,779 A | 2/1991 | Sugino et al. | |
| 5,526,422 A | 6/1996 | Keen | |
| 6,208,331 B1 | 3/2001 | Singh et al. | |
| 6,404,447 B1 * | 6/2002 | Kitagawa | 715/867 |

FOREIGN PATENT DOCUMENTS

| | | |
|---|---|---|
| EP | 0961454 | 12/1999 |
| JP | 04-365118 | 12/1992 |
| JP | 9160720 | 6/1997 |
| JP | 11085401 | 3/1999 |
| JP | 2000-194504 | 7/2000 |
| JP | 2004-265383 | 9/2004 |
| JP | 2004265383 A * | 9/2004 |
| JP | 2005301569 | 10/2005 |

OTHER PUBLICATIONS

European Search Report relating to patent application No. EP09167371, dated Dec. 15, 2011.

* cited by examiner

*Primary Examiner* — Alexander Eisen
*Assistant Examiner* — Robin Mishler
(74) *Attorney, Agent, or Firm* — Renner, Otto, Boisselle & Sklar, LLP

(57) ABSTRACT

The present invention provides a device that will not force, if the situation permits, the user to abort his or her work entirely when the modes of operation are changed from cleaning into non-cleaning, or vice versa. An information display device includes: a display section; a touchscreen panel, which forms an integral part of the display section and which has an input area that is associated with the display area of the display section; an area locating section for determining, in response to a user's action on the input area, what partial area of the input area has been operated on as a result of the user's action, thereby generating a signal specifying that partial area; and a control section for instructing the display section to display a non-opaque pattern with some degree of transparency. In a cleaning mode for cleaning the input area, the display section displays the pattern on the display area, and the control section increases the degree of transparency of that pattern on the partial area in accordance with the signal specifying the partial area.

13 Claims, 8 Drawing Sheets

```
LIST OF TODAY'S CONSULTATIONS (MORNING OF JUNE 15)    2

9:00-9:30  松下一郎      9:30-10:00  松下三郎
    9:00-9:30  松下二郎      9:30-10:00  松下四郎
    9:00-9:30  * * * *       9:30-10:00  * * * *
    9:00-9:30  * * * *       9:30-10:00  * * * *
    9:00-9:30  * * * *       9:30-10:00  * * * *
    9:00-9:30  * * * *      10:00-10:30  * * * *
    9:00-9:30  * * * *      10:00-10:30  * * * *
```

(a)

(b)

SCREEN CLEANING HAS FINISHED.
EXIT NOW?

YES    NO

*FIG.13*
(a) 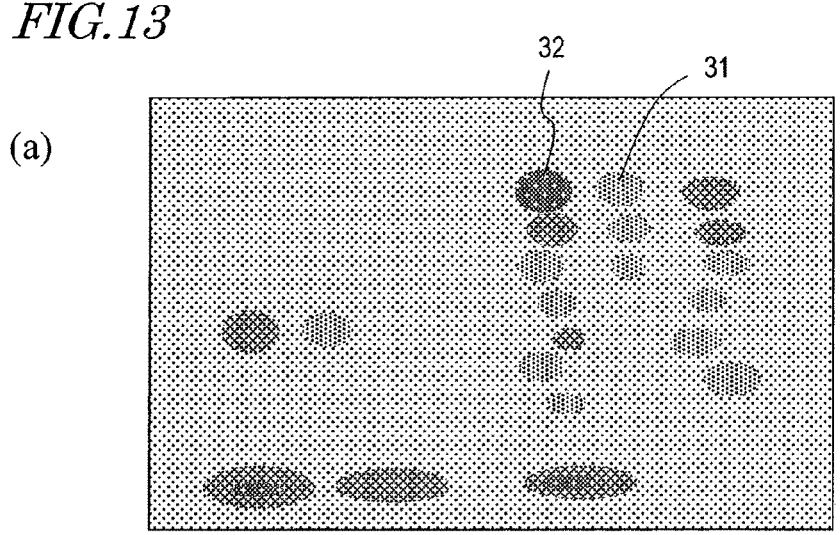
(b) 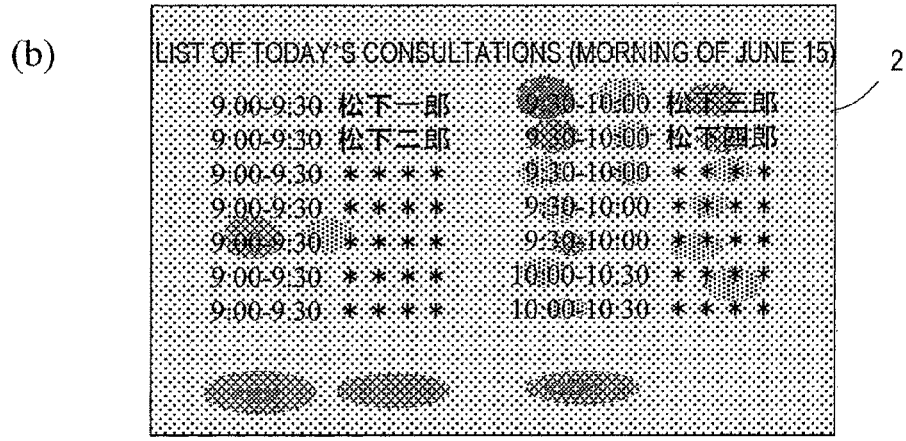
*FIG.14*
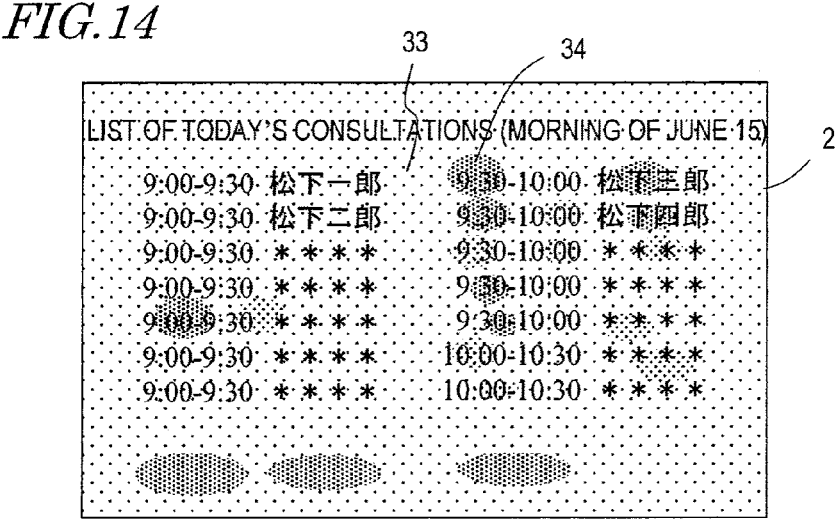

CLEANING MODE FOR INFORMATION DISPLAY DEVICE WITH TOUCHSCREEN

TECHNICAL FIELD

The present invention relates to an information display device with a touchscreen panel that forms an integral part of the display section thereof.

BACKGROUND ART

Recently, mobile information terminal devices such as PDAs and tablet personal computers have become increasingly popular and widespread. For such a mobile information terminal device, it is difficult to provide a keyboard or a mouse as its input device in order to increase its handiness and to meet the demand for size and weight reduction. That is why many of those devices use a touchscreen panel (which is sometimes called simply a "touchscreen"), including transparent thin film electrodes, as its display section (such as an LCD panel) so as to allow the user to operate the panel with a stylus or his or her finger.

Although it is easy to operate the machine with fingers, the display section soon gets dirty so much as to decrease the visibility of the display section. What is worse, the dirty display section has bacteria and is not hygienic. For that reason, if such an information display device needs to be used in a medical facility such as a hospital, the display section thereof should be cleaned and disinfected on a regular basis.

However, as the touchscreen panel is a transparent sheet, the dirt can not be seen so easily that it is usually difficult for a general user to decide when to clean it. Also, even after he or she has cleaned the screen, he or she is often still not sure if the dirt, dust or fingerprints have been removed from the screen sufficiently.

In order to overcome these problems, Patent Document No. 1 proposes the following method.

Specifically, Patent Document No. 1 discloses a technique for switching to a cleaning mode automatically when the number of times the touchscreen panel has been touched with a finger, which is counted by a counting means, reaches a predetermined number.

In the cleaning mode, the entire screen of the display section is displayed in a single color and the wiped and cleaned part is detected and has that colors erased or its colors changed into another one, thereby letting the user know what parts have been wiped.

Citation List

Patent Literature
  Patent Document No. 1: Japanese Patent Application Laid-Open Publication No. 2004-265383

SUMMARY OF INVENTION

Technical Problem

According to aforementioned Patent Document No. 1, when the cleaning mode is entered, the image that has been presented by then is still visible. However, as the cleaning advances, more and more portions of that image are painted in another color to be invisible. Or when the cleaning mode is entered, the entire screen of the display section is painted in a single color. In any case, the image that has been presented disappears. That is why even if the user has been working on some application before the cleaning mode is entered, he or she must abort that work entirely.

In other words, the user should understand how the normal operation mode and the cleaning mode work respectively and switch those modes one into the other. For that reason, even if he or she knows that it's about time to get the cleaning done after having entered the normal operation mode, he or she will hesitate to change the modes into the cleaning mode.

It is therefore an object of the present invention to provide a device that will not force, if the situation permits, the user to abort his or her work entirely when the modes of operation are changed from cleaning into non-cleaning, or vice versa.

Solution to Problem

An information display device according to the present invention includes: a display section; a touchscreen panel, which forms an integral part of the display section and which has an input area that is associated with the display area of the display section; an area locating section for determining, in response to a user's action on the input area, what partial area of the input area has been operated on as a result of the user's action, thereby generating a signal specifying that partial area; and a control section for instructing the display section to display a non-opaque pattern with some degree of transparency. In a cleaning mode for cleaning the input area, the display section displays the pattern on the display area, and the control section increases the degree of transparency of that pattern on the partial area in accordance with the signal specifying the partial area.

The control section may keep a record of integrated running time. On sensing the integrated running time exceed a predetermined value, the control section may get the pattern displayed on the display area.

On sensing the integrated running time exceed the predetermined value, the control section may instruct the display section to display a message saying that the device is going to switch to the cleaning mode, and then may get the display section to display the pattern.

The control section may keep a record of, as the integrated running time, at least one of an overall running time since the start-up of the device, the amount of time that has passed since the cleaning mode ended last time, and the amount of time that has passed since any of multiple users logged on this device in a situation where they are allowed to log on individually.

On detecting a change of the users, the control section may get the pattern displayed on the display section.

If multiple users are allowed to use this information display device by logging on individually, the control section may detect a change of the users by sensing any of the multiple users log on, sensing the device be removed from a cradle on which this device is supposed to be mounted when not used, or sensing a change of batteries.

When the device is going to switch to the cleaning mode, the display section may superimpose the pattern on an image that is presented on the display area thereof so that the image can still be seen to the user through the pattern.

The control section may execute an application program that runs in response to the user's action on the input area. The display section may superimpose the pattern on the window of the application program that is running when the device is going to switch to the cleaning mode.

When the cleaning mode is entered, the control section may stop the application program from running in response to the user's action.

The information display device may further include a counting section for counting, on a partial area basis, the frequency of the user's actions in a non-cleaning mode that is different from the cleaning mode. When the cleaning mode is going to be entered, the control section may change, on a partial area basis, the degrees of transparency of the pattern to be displayed initially on the display area according to the frequency that has been counted for each partial area.

The information display device may further include a storage section that stores information about the frequency that has been counted by the counting section on a partial area basis.

The input area may include a first partial area and a second partial area. If the user is taking action on the first partial area but not on the second partial area, then the pattern on the first partial area, of which the degree of transparency has been increased, and the pattern on the second partial area, of which the degree of transparency has not been increased, may be distinguishable from each other.

If a ratio of the partial area, on which the degree of transparency of the pattern has been increased, to the overall display area becomes equal to or higher than a predetermined value, the control section may end the cleaning mode.

The information display device may further include a storage section that stores, every time the cleaning mode is entered, information about whether the cleaning mode has ended or not.

Advantageous Effect of Invention

The present invention provides an information display device that not only can clean the dirt on the touchscreen panel uniformly but also does not force the user to abort his or her work entirely when the modes of operation are changed from a non-cleaning mode into a cleaning mode, or vice versa.

BRIEF DESCRIPTION OF DRAWINGS

[FIG. 13] FIG. 13(*a*) illustrates an example of a dirt pattern according to the second preferred embodiment and FIG. 13(*b*) illustrates the dirt pattern shown in FIG. 13(*a*) that is superimposed on the window of the application program running as shown in FIG. 7.

[FIG. 14] Illustrates what may be displayed during the cleaning.

DESCRIPTION OF EMBODIMENTS

Hereinafter, preferred embodiments of an information display device according to the present invention will be described with reference to the accompanying drawings. In the following description, a tablet information display device will be described as an example of an information display device according to the present invention. It should be noted that an information display device with the function of keeping up telecommunications with an external device will also be referred to herein as an "information terminal device".

Embodiment 1

Figure 1:
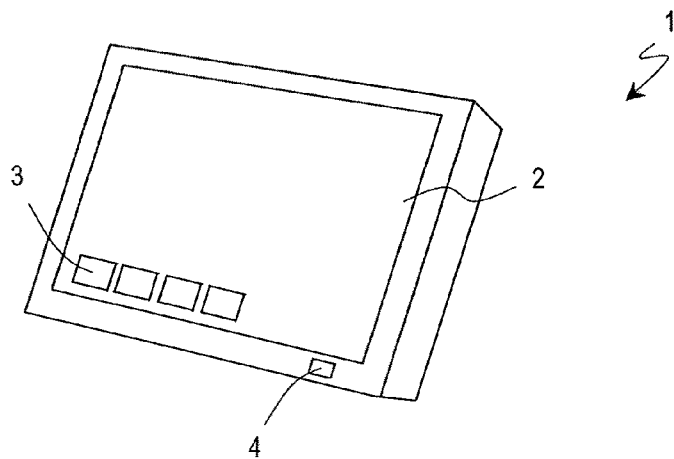
[FIG. 1] Illustrates the appearance of a tablet information terminal device 1 as a first specific preferred embodiment of the present invention.

FIG. 1 illustrates the appearance of a tablet information terminal device 1 as a specific preferred embodiment of the present invention. In this Preferred embodiment, the information terminal device 1 is connected to the information system of a hospital either wirelessly or with telecommunications lines and is used for doctors, nurses and other staffs to check out the patient's clinical records and the date of his or her next consultation with the doctor.

The information terminal device 1 includes a display section 2, a touchscreen panel 3, and a power switch 4.

The display section 2 may be a liquid crystal display (LCD) with a lot of liquid crystal cells.

The touchscreen panel 3 forms an integral part of the display section 2 and is arranged on the surface of the display section 2 so as to face the user. The touchscreen panel 3 has an input area and allows the user to operate the machine by touching a part of the input area with his or her finger, for example.

For example, if the display area of the display section 2 and the input area of the touchscreen panel 3 overlap with each other, then the display area of the display section 2 and the location of entry on the touchscreen panel 3 can be associated with each other. Specifically, by sensing exactly what partial area of the input area has been touched with the user's finger, the touchscreen panel 3 generates a signal specifying that partial area. Based on this signal, the information terminal device 1 locates the part of the display area of the display section 2 that has been touched by the user and carries out processing by regarding an image displayed in that part of the display area as a selected portion. It should be noted that a capacitance touchscreen panel 3 that is sensitive to a variation in charge is adopted.

The power switch 4 is arranged somewhere on the housing.

Normally, the user uses this information terminal device 1 by turning the power switch 4 ON, holding the body with one hand, and touching on the touchscreen panel 3 with a finger of the other hand to perform an input operation.

Figure 2:
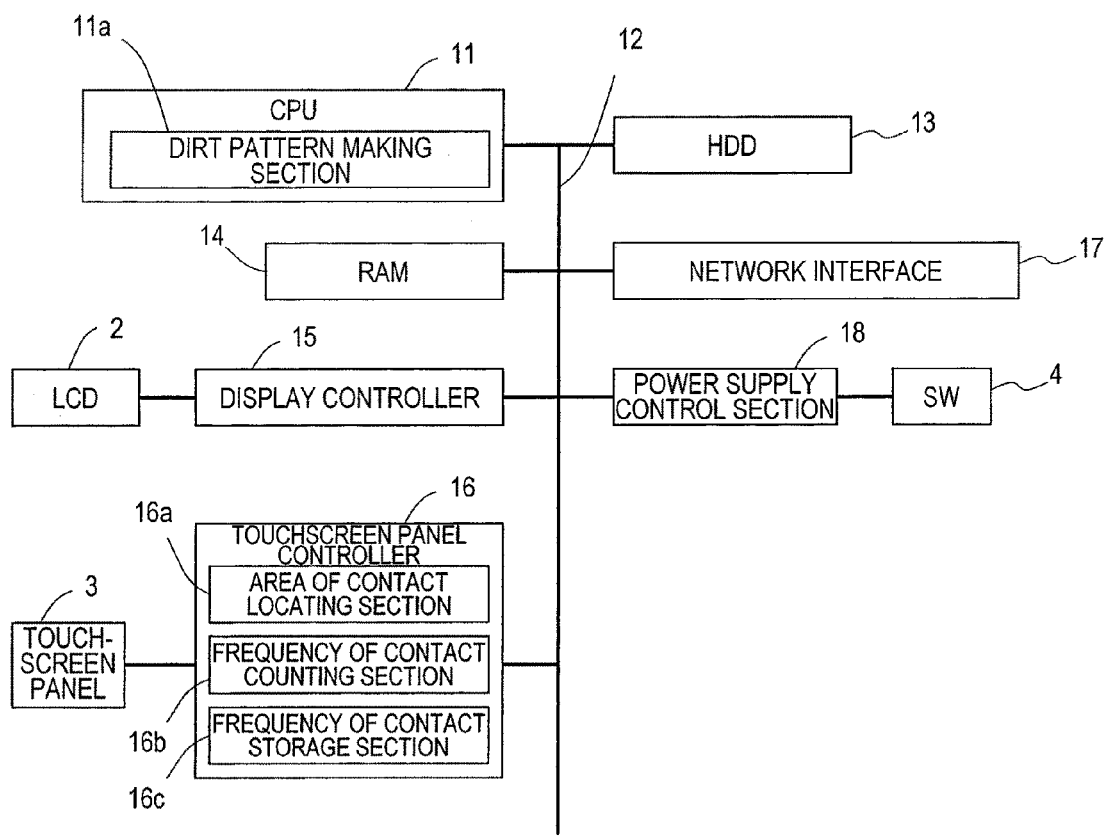
[FIG. 2] A block diagram illustrating an electrical configuration for the information terminal device 1 of the first preferred embodiment.

FIG. 2 is a block diagram illustrating an electrical configuration for the information terminal device 1 of this preferred embodiment. In FIG. 2, the CPU 11 is a processor that controls the overall processing of this information terminal device 1. The CPU 11 loads an operating system (OS) and various application programs, which are stored on a hard disk drive (HDD) 13, into a main memory (RAM) 14 by way of a system bus 12 for exchanging information, and executes them.

By executing the program on the RAM, the CPU 11 functions as a dirt pattern making section 11a as will be described later.

The display controller 15 transforms the image data, which has been generated by the OS or the application program, into a display signal and then outputs it to the display section (LCD) 2.

The touchscreen panel controller 16 senses a change on the touchscreen panel 3 and notifies the CPU 11 of that change either directly or by performing the processing to be described later. The touchscreen panel controller 16 functions as an area of contact locating section 16a, a frequency of contact counting section 16b and a frequency of contact storage section 16c as will be described later.

The network interface 17 is a terminal or an RF communications unit to be connected to a local area network (LAN). Through this network interface 17, information may be collected from a data server (not shown) that is also connected to the same LAN or a log indicating that the cleaning mode (to be described later) has ended may be output to a PC that is also connected to the same LAN.

The power supply control section 18 either supplies or shuts off power to/from the respective components by turning the power switch 4.

Next, it will be described how to operate the touchscreen panel 3 according to this preferred embodiment.

Figure 3:
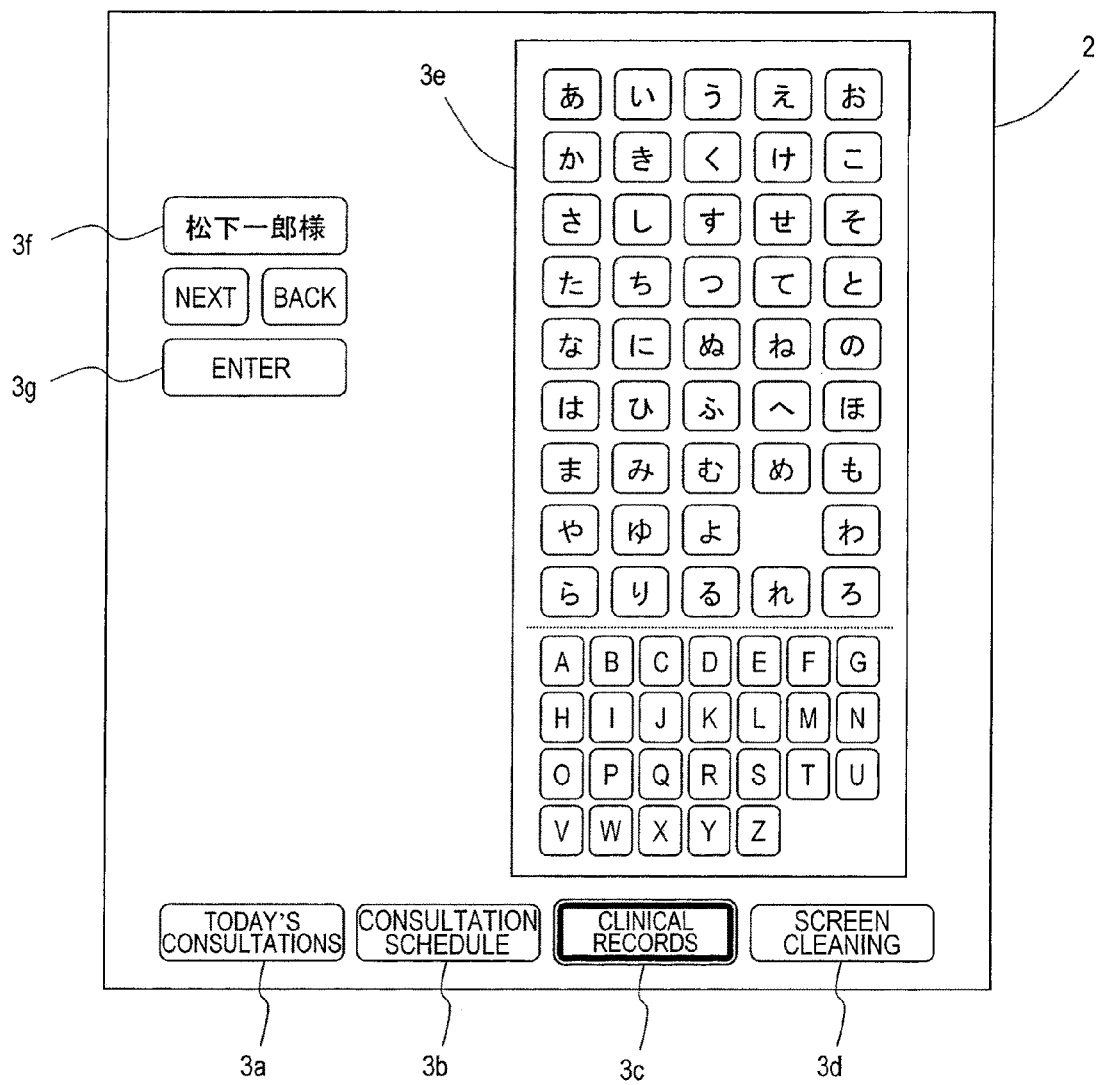
[FIG. 3] Illustrates an exemplary configuration for the touchscreen panel 3 of the information terminal device 1 of the first preferred embodiment.

FIG. 3 illustrates an exemplary configuration for the touchscreen panel 3 of the information terminal device 1 of this preferred embodiment. As described above, in this preferred embodiment, the information terminal device 1 may be used in an information system for a hospital.

On the display area of the display section 2, shown are operation keys 3a to 3c to allow the user to select one of service menu options available from the hospital's information system. In the example illustrated in FIG. 3, the menu option "clinical record" is now selected in response to the user's touch on the operation key 3c of the touchscreen panel 3.

In this state, a character input pad 3e that prompts the user to enter the patient's name is now displayed on the screen. For example, if the user touches the keys "ま(which is a Japanese hiragana letter that reads MA)", "つ (TSU)", "し (SHI)", "た (TA)", "い (I)", "ち (CHI)", "ろ (RO)", and "う (U)" on the character input pad 3e, then the patient's name is displayed in the name area 3f. And if the ENTER key 3g is touched, the patient's clinical record will be displayed.

It should be noted that the other operation key 3d is a CLEANING key that is used to change the modes of operation of the touchscreen panel 3 to a cleaning mode intentionally as will be described later.

Hereinafter, it will be described with reference to FIG. 4 through 11 exactly how this information terminal device 1 operates.

Figure 4:
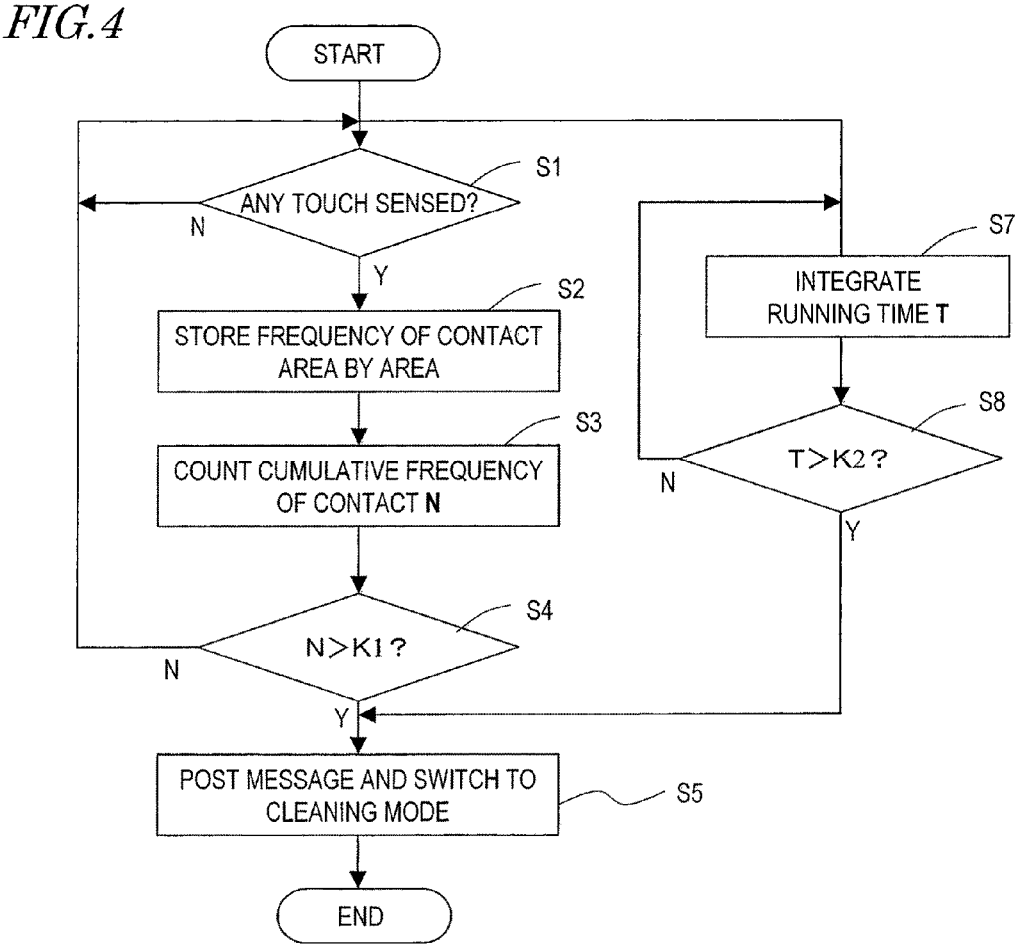
[FIG. 4] A flowchart illustrating how the information terminal device 1 of the first preferred embodiment operates in a normal (use) mode.

FIG. 4 is a flowchart illustrating how the information terminal device 1 of this preferred embodiment operates in a normal (use) mode. As used herein, the "operation in the normal mode" refers mainly to the operation of the touchscreen panel controller 16 in a situation where the information terminal device 1 uses the hospital's information system.

First of all, in Step S1, the touchscreen panel controller 16 senses a touch on the touchscreen panel 3. Then, in the next processing step S2, the area of contact locating section 16a determines exactly what area of the touchscreen panel 3 has been touched on. On the other hand, the frequency of contact counting section 16b counts (or adds) the frequency of contact on an area-by-area basis and gets the frequency stored in the frequency of contact storage section 16c.

Next, in Step S3, the cumulative frequency of contact N is obtained. Then, in Step S4, it is determined whether or not the cumulative frequency of contact N has reached a predetermined value K1. If the answer to the query of Step S4 is NO (i.e., if N<K1), then the process goes back to Step S1 to perform the same series of processing steps S1 through S3 all over again. On the other hand, if the answer to the query of Step S4 is YES (i.e., if N≧K1), then that information is conveyed to the CPU 11. In that case, in the next processing step S5, the CPU 11 composes a message that says "screen needs cleaning" and gets that message posted on the display section 2. After that, the modes of operation of the information terminal device 1 are switched from the normal mode into the cleaning mode.

Figure 5:
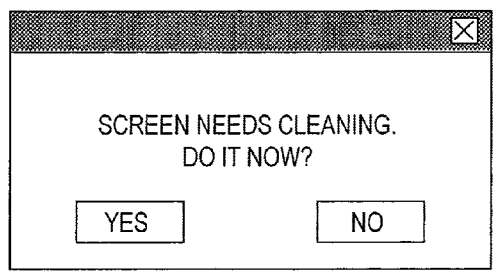
[FIG. 5] Shows an exemplary message that may be posted on the display section 2.

FIG. 5 shows an exemplary message that may be posted on the display section 2. It should be noted that the CPU 11 could, but does not have to, compose a different message every time. Alternatively, data about various messages may be stored on the HDD 13 or the RAM 14 in advance and then one of them may be retrieved and displayed by the CPU 11.

Optionally, the timing to post such a message could also be determined by performing the processing steps S7 and S8. Specifically, in that case, the integrated running time of the information terminal device 1 is calculated and stored as an integrated value T in Step S7 and then it is determined in the next processing step S8 whether or not the integrated value T has reached a predetermined value K2. As used herein, the "running time" may be the overall running time since the start-up of the information terminal device 1, the amount of time that has passed since any of multiple users logged on this device in a situation where they are allowed to use this information terminal device 1 by logging on individually, or the amount of time that has passed since the cleaning mode ended last time. The integrated value T of these times is calculated by the CPU 11. And the CPU 11 may determine, based on the running time, whether or not the device needs to switch to the cleaning mode by comparing the integrated value T to the predetermined value K2.

In the preferred embodiment just described, it is determined, based on the cumulative frequency of contact on the touchscreen panel 3, whether or not the screen needs cleaning now. However, the present invention is in no way limited to that specific preferred embodiment. Alternatively, it may also be determined that the screen needs cleaning and a message that prompts the user to do cleaning may be displayed when the highest frequency of contact among various areas is found to be more than a predetermined setting.

If such a message (or warning) that prompts the user to do cleaning is displayed as described above, it is easy for him or her to decide when to start cleaning.

However, the user could also change the modes into cleaning, no matter whether the information terminal device 1 is displaying such a cleaning alert or not. For example, if the user feels that obviously this device needs cleaning, then he or she can enter the cleaning mode by touching on the CLEANING key 3d. In that case, the cleaning may be done by manually pressing a cloth impregnated with a disinfectant against the touchscreen panel 3 or operation buttons, or wiping them with such a cloth.

Figure 6:
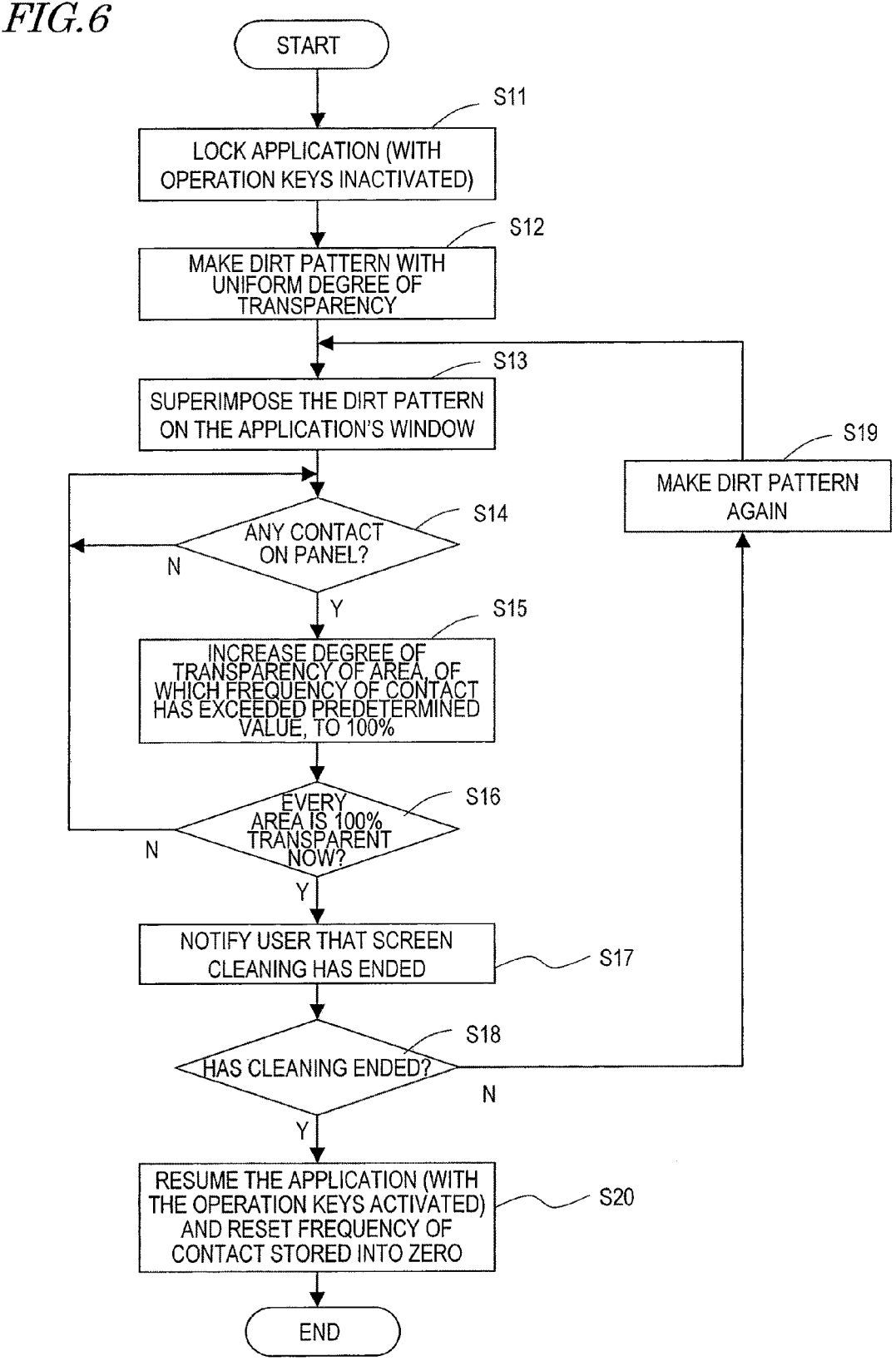
[FIG. 6] A flowchart illustrating a series of processing steps to be performed by the information terminal device 1 of the first preferred embodiment in the cleaning mode.

FIG. 6 is a flowchart illustrating a series of processing steps to be performed by the information terminal device 1 of this preferred embodiment in the cleaning mode.

The cleaning mode is entered by either touching the "YES" key shown in FIG. 5 or touching the screen cleaning key 3d shown in FIG. 3 at an arbitrary timing while the power of the information terminal device 1 is ON. Alternatively, the cleaning mode could also be entered when the user touches on an icon (not shown) to start a cleaning mode utility, which may be shown at the bottom of the display section 2. Still alternatively, the amount of time that has passed since the cleaning mode ended last time may always be measured with a timer and when a predetermined amount of time passes, the message shown in FIG. 5 may be displayed automatically to prompt the user to do cleaning.

The following series of processing steps are carried out by the CPU 11 either in response to a signal supplied from the touchscreen panel controller 16 to indicate what partial area has been touched or based on the information about the frequency of contact.

In the example to be described below, the CPU 11 is supposed to be executing at least one program (such as an application program) in the normal mode and the modes of operation are supposed to be changed into the cleaning mode while the CPU 11 is executing such a program.

First of all, in Step S11, the CPU 11 locks the application program that is running when the switch to the cleaning mode is instructed, thereby prohibiting the user from operating on the application program with any operation key of the touchscreen panel 3 on the display section 2.

Figures 7, 8:
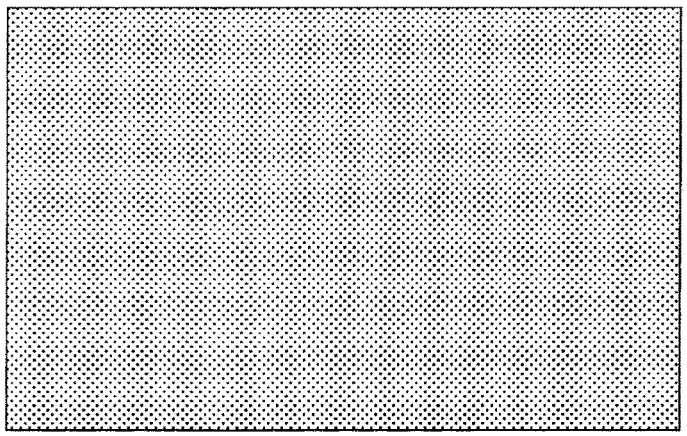
[FIG. 7] Illustrates what may be displayed on the display section 2 when the user is prohibited from operating on the application program.
[FIG. 8] FIG. 8(*a*) illustrates an example of a dirt pattern and FIG. 8(*b*) illustrates the dirt pattern shown in FIG. 8(*a*) that is superimposed on the window of the application program running as shown in FIG. 7.

FIG. 7 illustrates what may be displayed on the display section 2 when the user is prohibited from operating on the application program. Specifically, in the situation illustrated in FIG. 7, a list of reserved consultations is displayed in response to a touch on the operation key 3a (today's consultations) on the window shown in FIG. 3 and every key to be manipulated with a touch has already disappeared from the screen. Thus, the user can no longer operate on the application program. It should be noted that to "lock" the application program means just prohibiting the user from operating on the program with operation keys. That is why he or she can continue any other operation unless the operation keys are used.

Next, in Step S12 shown in FIG. 6, the dirt pattern making section 11a makes a dirt pattern. FIG. 8(a) illustrates an example of such a dirt pattern, which has a uniform degree of transparency over the entire display area of the display section 2. In this case, the degree of transparency may be set to any value unless the pattern is totally opaque. The degree of transparency may be either a preset one or determined on an area-by-area basis according to the frequency of contact as already described with reference to FIG. 4.

That is to say, when the cleaning mode is entered, the CPU 11 accesses the touchscreen panel controller 16 and determines the current degree of transparency according to the frequency of contact that is stored in the frequency of contact storage section 16c. Specifically, if the frequency of contact is high, the degree of transparency is determined to be low (i.e., the degree of opacity is high). On the other hand, where the frequency of contact is low, the degree of transparency is determined to be high (i.e., the degree of opacity is low). In the following example, the dirt pattern yet to be cleaned is supposed to have a degree of transparency of 50%.

It should be noted that the dirt pattern making section 11a could, but does not have to, make a different dirt pattern every time. Alternatively, image data representing various dirt patterns with mutually different degrees of transparency may be stored on the HDD 13 or the RAM 14 in advance and the CPU 11 may retrieve any of the image data according to the current degree of transparency determined.

Next, in Step S13, the CPU 11 displays the dirt pattern thus made as a superimposed image on the window of the application program running on the display section 2. Such a state is illustrated in FIG. 8(b), which illustrates the dirt pattern shown in FIG. 8(a) that is superimposed on the window of the application program running as shown in FIG. 7. That is to say, the window of the application program running is still displayed but is represented as if the entire screen is uniformly dirty. However, since the dirt pattern is not opaque, the user can still see, through the pattern, the window of the application program running, even though the dirt pattern is now superimposed on that window.

Next, in Step S14, the touchscreen panel controller 16 determines whether or not any contact has been made on the panel. If the panel has been cleaned, it has naturally been touched. And the area of contact locating section 16a senses such contact on the panel on an area-by-area basis. The size of the "area" may be defined arbitrarily unless the area is too big. For example, each one of the pixels that form the display area may be defined as a unit area. Or a number of pixels, of which the combined area is approximately as large as the average area of a human fingertip, may also be defined as a unit area. However, if the unit area were too large, then it would be meaningless to perform the processing steps S15 and S16 (to be described later) separately from each other. That is why four or more areas are preferably provided.

Figure 9:
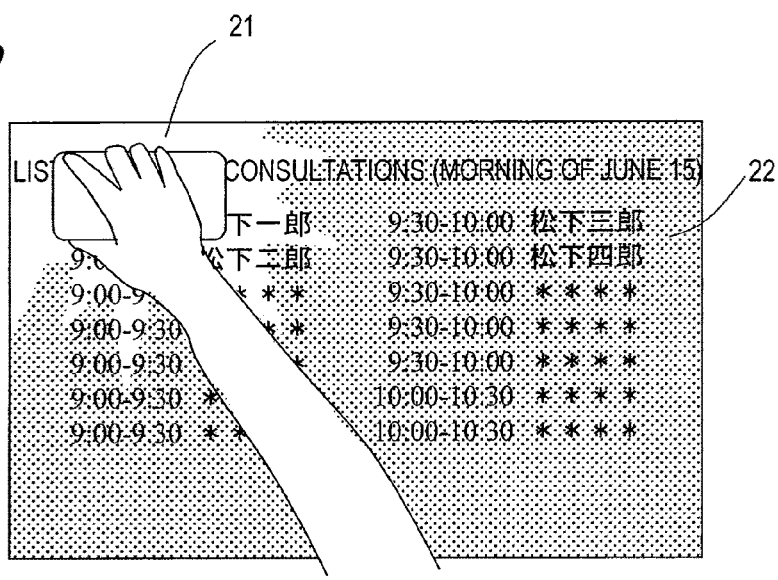
[FIG. 9] Illustrates what may be displayed during the cleaning.

The information about the contact that has been sensed on the panel is conveyed to the CPU 11 as needed. Then, in the next processing step S15, the dirt pattern is modified so as to increase the degree of transparency on an area-by-area basis according to the frequency of contact, and then displayed on the display section 2. FIG. 9 illustrates what may be displayed during the cleaning. In FIG. 9, the display area of the display section 9 is split into an area 21 that has already been cleaned by the user who has wiped the touchscreen panel with a cloth, for example, and the other area 22 that has not been cleaned yet. As for the cleaned area 21, the degree of transparency of the dirt pattern superimposed has been increased to the maximum (e.g., 100% in this preferred embodiment). On the other hand, as for the area 22 yet to be cleaned, the dirt pattern superimposed still has a degree of transparency of 50%. Thus, the user can see, at a glance, which area has not been cleaned yet, and therefore, will never forget to clean the entire screen. In addition, the efficiency of cleaning can be increased as well.

Alternatively, it may also be determined, by the frequency of contact, whether or not the screen has been cleaned entirely. For example, it is not until each area is touched on (or wiped) twice that its degree of transparency may be determined to be 100%. Next, in Step S16, it is determined whether or not the entire area now has a degree of transparency of 100%.

Figure 10:
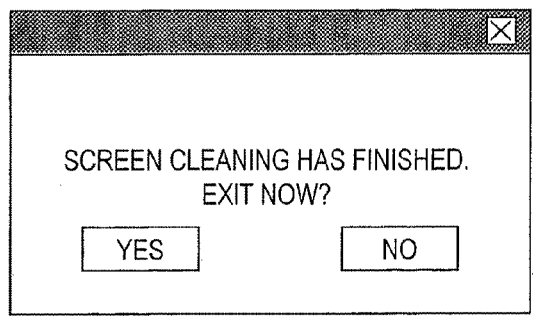
[FIG. 10] Shows an example of a message to be posted on the display section 2 when the cleaning ends.

When the degree of transparency reaches 100%, a message that says the screen cleaning has ended is displayed on the display section 2 in the next processing step S17. FIG. 10 shows an example of such a message to be displayed on the display section 2 when the cleaning ends.

In the next processing step S18, the user is asked if he or she'd like to finish cleaning now. If the answer is NO (i.e., if the "NO" button is touched on the dialog box shown in FIG. 10), then the CPU 11 makes another dirt pattern in the next processing step S19 and performs the same series of processing steps S13 through S19 all over again. In this case, the degree of transparency of the dirt pattern may also be 50% as in the first cleaning process or increased to 70%, which is higher than in the first cleaning process.

Figure 11:
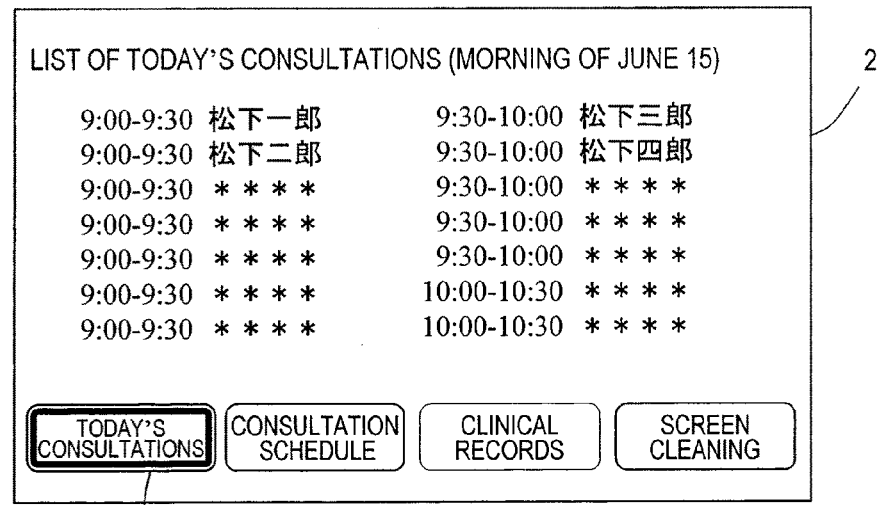
[FIG. 11] Illustrates how the display section looks when the application program is up and running again.

On the other hand, if the user decides to finish the cleaning process in Step S18 (i.e., if the "YES" button is touched on the dialog box shown in FIG. 10), then the process advances to the next processing step S20, in which the CPU 11 resumes executing the application program and unlocks the application program at the same time. Specifically, the operation keys are displayed on the display section 2 and activated again. Also, the frequency of contact stored in the frequency of contact storage section 16c is reset into zero. FIG. 11 illustrates how the display section looks when the application program is up and running again. As shown in FIG. 11, when the application program resumes running, the operation keys (including the "today's consultations" key 3a) appear again under the list of reserved consultations. By tapping these operation keys, the user starts operating the information terminal device 1 all over again.

As described above, according to this preferred embodiment, the user can see, at a glance, what part of the panel has already been cleaned. In addition, since the dirt pattern superimposed is semitransparent, the user can get the cleaning done while still looking at the window of the application program running. Thus, the cleaning process would not interfere with his or her business seriously.

In the preferred embodiment described above, the touchscreen panel controller 16 is supposed to include the frequency of contact counting section 16b and the frequency of contact storage section 16c. However, those functions are not always necessary. If those functions are omitted, the dirt pattern made by the dirt pattern making section 11a may always have the same degree of transparency irrespective of the frequency of contact. But if some area has been wiped with a cloth in the cleaning mode, the degree of transparency of that area may be increased to 100%, for example.

According to the preferred embodiment described above, even if the modes of operation are changed from the normal mode, in which an application program is running, into the cleaning mode, a non-opaque (e.g., semitransparent) dirt pattern is superimposed on the window of the application program running. Although prohibited from operating on the application program, the user can still check out the contents of the application program even during the cleaning mode. That is to say, since the user can get the cleaning done while checking out the contents of the application program, he or she does not have to abort entirely the application program that he or she has been using.

It should be noted that the messages to be displayed are also superimposed on the window of the application program, and therefore, preferably displayed in a non-opaque state.

Embodiment 2

In the first preferred embodiment described above, the dirt pattern is supposed to have the same degree of transparency over the entire screen of the touchscreen panel. According to a second preferred embodiment of the present invention, however, the degree of transparency is varied on an area-by-area basis according to the frequency of contact in the normal (use) mode. Generally speaking, an area to be touched on frequently gets dirty easily but an area to be rarely touched on does not get dirty so easily. That is why such an area to get dirty easily has its degree of transparency decreased to make its dirtiness even more apparent and eventually get the cleaning done more efficiently.

The common features between the first preferred embodiment and this preferred embodiment, which have already been described with reference to FIGS. 1 through 5 and FIG. 7, will not be described again to avoid redundancies.

Figure 12:
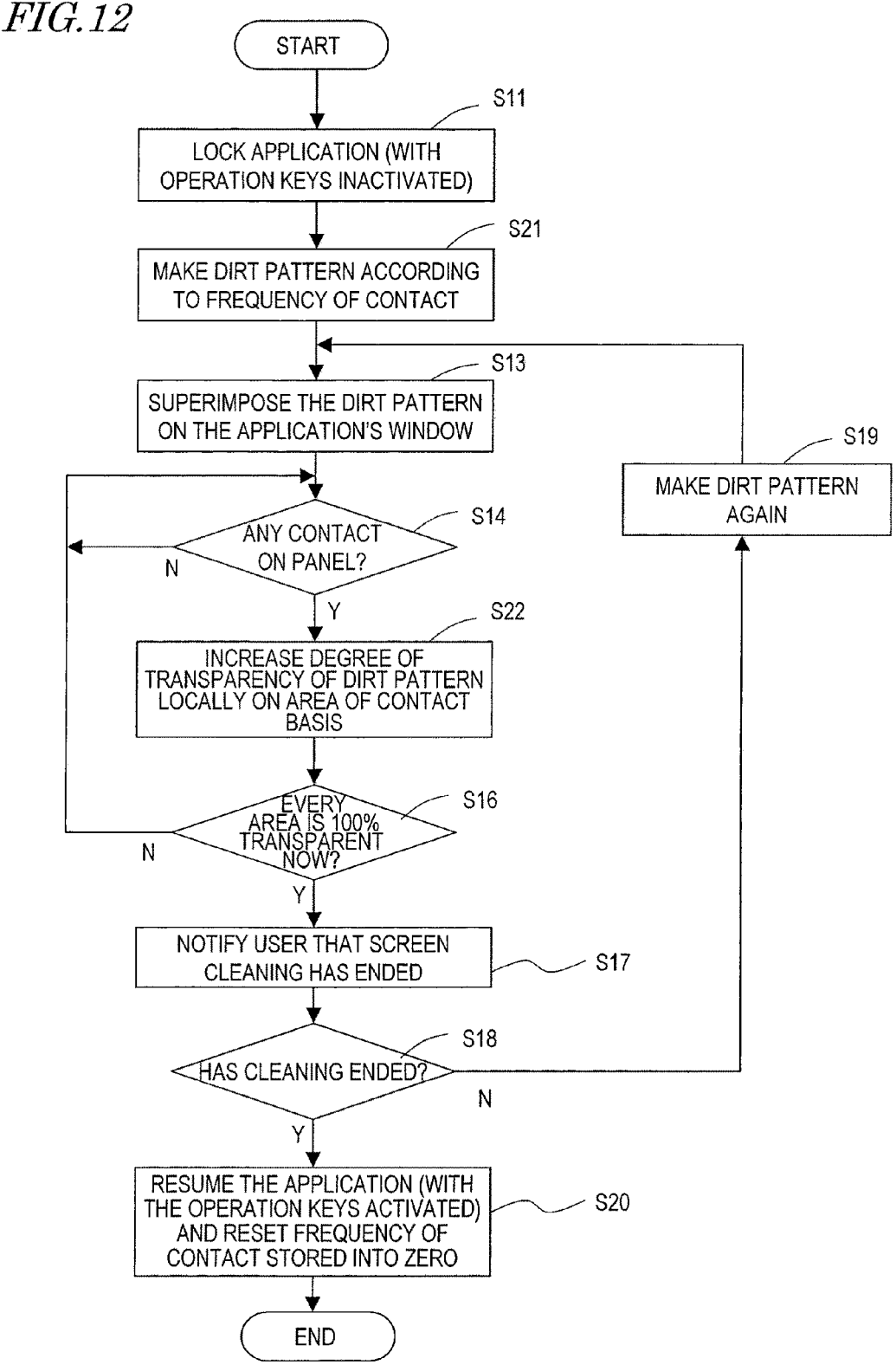
[FIG. 12] A flowchart showing a series of processing steps to be performed by the information terminal device 1 of a second preferred embodiment of the present invention in the cleaning mode.

FIG. 12 is a flowchart showing a series of processing steps to be performed by the information terminal device 1 of this preferred embodiment in the cleaning mode. The information terminal device 1 of this preferred embodiment operates differently from the counterpart of the first preferred embodiment described above in the processing step S21 of making a dirt pattern according to the frequency of contact and the processing step S22 of increasing the degree of transparency of the dirt pattern locally on an area of contact basis.

Hereinafter, the flow of the cleaning process of this preferred embodiment will be described with reference to the flowchart shown in FIG. 12. First of all, in Step S11, the CPU 11 locks the application program being executed and prohibits the user from operating on the application program with the operation keys that are displayed on the touchscreen panel 3 on the display section 2.

This is the same state as the one illustrated in FIG. 7 that has already been referred to for the first preferred embodiment. Next, in Step S21, the dirt pattern making section 11a makes a dirt pattern such as the one illustrated in FIG. 13(a). This dirt pattern is semitransparent over the entire screen but has varying degrees of transparency from one area to another.

Such a difference in the degree of transparency is determined on an area-by-area basis by the frequency of contact as already described with reference to FIG. 4.

That is to say, as soon as the cleaning mode is entered, the CPU 11 accesses the touchscreen panel controller 16, gets the frequency of contact that is stored in the frequency of contact storage section 16c on an area-by-area basis, and then determines the degree of transparency of each area according to the frequency of contact. Specifically, an area with a high frequency of contact should have a low degree of transparency (i.e., a high degree of opacity) but an area with a low frequency of contact should have a high degree of transparency (i.e., a low degree of opacity). Then, a portion 32 of the pad 3e (see FIG. 3) representing a letter key to be touched on frequently is displayed in a darker color, while an adjacent portion 31 on the right-hand side of the portion 32 is displayed in a lighter color. In this manner, the user can see, at a glance, what part of the touchscreen panel is relatively dirty and what part is not when the cleaning process is started. As a result, the touchscreen panel can be cleaned more efficiently.

Next, in Step S13, the CPU 11 displays the dirt pattern thus made as a superimposed image on the window of the application program running on the display section 2. Such a state is illustrated in FIG. 13(b), which illustrates the dirt pattern shown in FIG. 13(a) that is superimposed on the window of the application program running as shown in FIG. 7. That is to say, the varying degrees of dirtiness on the screen are represented while the window of the application program running is still displayed.

Subsequently, in Step S14, the touchscreen panel controller 16 determines whether or not any contact has been made on the panel. If the panel has been cleaned, it has naturally been touched. And the area of contact locating section 16a senses such contact on the panel on an area-by-area basis. The size of each area may be defined as already described for the first preferred embodiment.

The information about the contact that has been sensed on the panel is conveyed to the CPU 11 as needed. Then, in the next processing step S22, the dirt pattern is modified so as to increase the degree of transparency on an area-by-area basis according to the frequency of contact, and then displayed on the display section 2. FIG. 14 illustrates what may be displayed during the cleaning. In FIG. 14, an area 33 in which the cleaning process has advanced sufficiently (i.e., which has a high frequency of contact) has a high degree of transparency, but an area 34 in which the cleaning process has not advanced sufficiently (i.e., which has a low frequency of contact) has a low degree of transparency. Thus, the user can see, at a glance, which area has not been cleaned yet, and can keep track of a detailed status of cleaning more visually. As a result, the efficiency of cleaning can be further increased.

Next, in Step S16, it is determined whether or not the entire area now has a degree of transparency of 100%.

After that, the processing steps S17 through S20 will be performed in quite the same way as in the first preferred embodiment, and the description thereof will be omitted herein.

As described above, the information terminal device of this preferred embodiment stores the frequency of contact on each area of the touchscreen panel in the normal mode. And when the cleaning mode is entered, a semitransparent dirt pattern, which has varying degrees of transparency according to the frequency of contact stored on an area-by-area basis, is superimposed on a program of the application program suspended. Also, in the cleaning mode, the degree of transparency of each area is increased as the frequency of contact (or wipes) on that area of the touchscreen panel increases as a result of cleaning. Consequently, the degree of dirtiness and the status of cleaning can be displayed on an area-by-area basis on the display section, and therefore, the entire screen of the display section can be cleaned uniformly.

In the preferred embodiment described above, a message notifying the user of the end of the screen cleaning is supposed to be displayed when the degree of transparency of the entire screen of the touchscreen panel 3 reaches 100%. However, such a message may also be displayed if the areas with a degree of transparency of 100% (i.e., cleaned areas) have a predetermined combined area or a predetermined percentage (of 97%, for example) when the user stops wiping the screen with a cloth, for example (more exactly when a predetermined amount of time passes after no contact is sensed anymore).

Furthermore, in the preferred embodiments described above, the date of cleaning, the name of the person who did the cleaning, the decision of the cleaning (which may be either "completed" or "aborted") and other cleaning stats may be saved as logs, and it may be determined, based on the contents of those logs, when to do the cleaning next time. Optionally, those logs may also include the time when the message prompting the user to switch to the cleaning mode was displayed and information about whether the cleaning mode has ended or not. Those logs may be retrieved by a PC connected to a LAN by way of the network interface 17 (see FIG. 2). And those logs may be saved on either the HDD 13 or the RAM 14, for example.

Furthermore, in the preferred embodiments described above, if the areas with a degree of transparency of 100% (i.e., the cleaned areas) account for a predetermined percentage or less of the entire screen, those areas may either have their degree of transparency further decreased or be painted in a contrasting color (e.g., the complementary color of the background color) to make those areas easily sensible.

In a situation where this information terminal device 1 is used by multiple users, the message notifying the new user that the device is going to switch to the cleaning mode may be displayed, and/or the device may actually switch to the cleaning mode, every time the change of users is detected. The change of users may be sensed by any of various methods. For example, if multiple users use this information terminal device 1 by logging on the device individually, the CPU 11 may detect the change of users by sensing one of them log on this device. Also, if, when not used, this information terminal device 1 is supposed to be mounted on a cradle to have its batteries charged, the removal of the device 1 from the cradle may be sensed, and thereby the change of users may be detected, by determining whether or not there is an externally applied voltage. Furthermore, when the batteries are changed, it may also be determined that the users have changed. By detecting the change of users by any of these methods, the device will switch to the cleaning mode and a dirt pattern will be superimposed on the window that has been displayed on the screen until then.

In the preferred embodiments described above, the touchscreen panel 3 is supposed to be a capacitance type. However, this is just an example. Examples of other known touchscreen sensors include a voltage sensing type that uses a resistive film, an infrared ray cut-off type for detecting the coordinates of a point where an incoming infrared ray has been cut off, and an electromagnetic induction type that allows the user to touch the screen with a special kind of stylus that can generate magnetic field and that makes the panel receive the electromagnetic energy and thereby locate the point of contact with the stylus.

Among other things, if a touchscreen panel of the electromagnetic induction type is used, the user's input could be received even without having the stylus make direct contact with the panel (i.e., even if the stylus is out of contact with the panel). Nevertheless, even if the user did not make the stylus contact with such an electromagnetic induction type touchscreen panel, the surface of the touchscreen panel could still get dirty with splashes of some chemicals, for example. That is why the present invention can be used effectively even in a touchscreen panel of such an electromagnetic induction type.

To make the user sense which area of the electromagnetic induction type touchscreen panel has been cleaned as shown in FIG. 9, the user may wipe the screen with the dedicated stylus wrapped with a cloth or using a dedicated cloth including a material that generates magnetic field.

Industrial Applicability

The present invention is applicable effectively to not only mobile information display devices but also fixed information display devices with a touchscreen panel such as an automatic teller machine (ATM) for a bank.

Reference Signs List

1 information terminal device (information display device with telecommunications function)
2 display section touchscreen panel
3*a*, 3*b*, 3*c*, 3*d*, 3*g* operation key
3*e* katakana pad
3*f* name area
3*g* ENTER key
4 power switch
11 CPU
11*a* dirt pattern making section
12 system bus
13 HDD
14 RAM (main memory)
15 display controller
16 touchscreen panel controller
16*a* area of contact locating section
16*b* frequency of contact counting section
16*c* frequency of contact storage section
17 network interface
18 power control section

The invention claimed is:

1. An information display device comprising:
a display section;
a touchscreen panel, which forms an integral part of the display section and which has an input area that is associated with the display area of the display section;
an area locating section for determining, in response to a user's action on the input area, what partial area of the input area has been operated on as a result of the user's action, thereby generating a signal specifying that partial area; and
a control section for instructing the display section to display a semitransparent pattern with some degree of transparency,
wherein in a cleaning mode for cleaning the input area,
the display section superimposes the pattern on an image that is presented on the display area thereof so that the image can still be seen to the user through the pattern, and
the control section increases the degree of transparency of that pattern on the partial area in accordance with the signal specifying the partial area.

2. The information display device of claim 1, wherein the control section keeps a record of integrated running time, and
wherein on sensing the integrated running time exceed a predetermined value, the control section gets the pattern displayed on the display area.

3. The information display device of claim 2, wherein on sensing the integrated running time exceed the predetermined value, the control section instructs the display section to display a message saying that the device is going to switch to the cleaning mode, and then gets the display section to display the pattern.

4. The information display device of claim 2, wherein the control section keeps a record of, as the integrated running time, at least one of an overall running time since the start-up of the device, the amount of time that has passed since the cleaning mode ended last time, and the amount of time that has passed since any of multiple users logged on this device in a situation where they are allowed to log on individually.

5. The information display device of claim 1, wherein on detecting a change of the users, the control section gets the pattern displayed on the display section.

6. The information display device of claim 5, wherein if multiple users are allowed to use this information display device by logging on individually,
the control section detects a change of the users by sensing any of the multiple users log on, sensing the device be removed from a cradle on which this device is supposed to be mounted when not used, or sensing a change of batteries.

7. The information display device of claim 1, wherein the control section executes an application program that runs in response to the user's action on the input area, and
wherein the display section superimposes the pattern on the window of the application program that is running when the device is going to switch to the cleaning mode.

8. The information display device of claim 7, wherein when the cleaning mode is entered, the control section stops the application program from running in response to the user's action.

9. The information display device of claim 1, further comprising a counting section for counting, on a partial area basis, the frequency of the user's actions in a non-cleaning mode that is different from the cleaning mode,
wherein when the cleaning mode is going to be entered, the control section changes, on a partial area basis, the degrees of transparency of the pattern to be displayed initially on the display area according to the frequency that has been counted for each said partial area.

10. The information display device of claim 9, further comprising a storage section that stores information about the frequency that has been counted by the counting section on a partial area basis.

11. The information display device of claim 1, wherein the input area includes a first partial area and a second partial area, and
wherein if the user is taking action on the first partial area but not on the second partial area, then the pattern on the first partial area, of which the degree of transparency has been increased, and the pattern on the second partial area, of which the degree of transparency has not been increased, are distinguishable from each other.

12. The information display device of claim 1, wherein if a ratio of the partial area, on which the degree of transparency of the pattern has been increased, to the overall display area becomes equal to or higher than a predetermined value, the control section ends the cleaning mode.

13. The information display device of claim 12, further comprising a storage section that stores, every time the cleaning mode is entered, information about whether the cleaning mode has ended or not.

* * * * *